US012599353B2

(12) United States Patent
Peng et al.

(10) Patent No.: US 12,599,353 B2
(45) Date of Patent: Apr. 14, 2026

(54) VISUALIZATION OF TOUCH PANEL TO OBJECT DISTANCE IN X-RAY IMAGING

(71) Applicant: Siemens Shanghai Medical Equipment Ltd., Shanghai (CN)

(72) Inventors: Xi Shuai Peng, Shanghai (CN); Jing Tai Cao, Shanghai (CN); Yun Zhe Zou, Shanghai (CN)

(73) Assignee: Siemens Shanghai Medical Equipment Ltd., Shanghai (CN)

( * ) Notice: Subject to any disclaimer, the term of this patent is extended or adjusted under 35 U.S.C. 154(b) by 164 days.

(21) Appl. No.: 18/685,606

(22) PCT Filed: Aug. 24, 2021

(86) PCT No.: PCT/CN2021/114386
§ 371 (c)(1),
(2) Date: Feb. 22, 2024

(87) PCT Pub. No.: WO2023/023956
PCT Pub. Date: Mar. 2, 2023

(65) Prior Publication Data
US 2024/0350105 A1     Oct. 24, 2024

(51) Int. Cl.
A61B 6/04          (2006.01)
A61B 6/00          (2006.01)
(Continued)

(52) U.S. Cl.
CPC ............... A61B 6/547 (2013.01); A61B 6/04 (2013.01); A61B 6/0407 (2013.01);
(Continued)

(58) Field of Classification Search
CPC ....... A61B 6/04; A61B 6/0407; A61B 6/4258; A61B 6/44; A61B 6/4405; A61B 6/4452; A61B 6/4464; A61B 6/4476; A61B 6/46; A61B 6/461; A61B 6/465; A61B 6/466; A61B 6/467; A61B 6/469; A61B 6/52; A61B 6/5205; A61B 6/5211; A61B 6/5258; A61B 6/5282; A61B 6/5294; A61B 6/54; A61B 6/547; A61B 6/58; A61B 6/582;
(Continued)

(56) References Cited

U.S. PATENT DOCUMENTS 7,260,426 B2 *  8/2007  Schweikard ............. A61B 6/12
                                                      600/407
7,433,503 B2 * 10/2008  Cherek ................. A61B 6/469
                                                      382/128
(Continued)

OTHER PUBLICATIONS

Feb. 14, 2022 (PCT) International Search Report and Written Opinion—App. PCT/2021/114386.

*Primary Examiner* — Allen C. Ho
(74) *Attorney, Agent, or Firm* — Banner & Witcoff, Ltd.

(57) ABSTRACT

Method and apparatus for visualization of a touch panel to object distance (TOD) in X-ray imaging. The method includes: obtaining a three-dimensional image of a to-be-detected subject that includes an object; determining a TOD; generating a first identifier at a position of a touch panel in the three-dimensional image; and generating a second identifier in the three-dimensional image, where a distance between the first identifier and the second identifier corresponds to the TOD.

18 Claims, 9 Drawing Sheets

(51) Int. Cl.

| | |
|---|---|
| *A61B 6/42* | (2024.01) |
| *A61B 6/46* | (2024.01) |
| *A61B 6/50* | (2024.01) |
| *A61B 6/58* | (2024.01) |

(52) U.S. Cl.
CPC .......... *A61B 6/4258* (2013.01); *A61B 6/4452* (2013.01); *A61B 6/465* (2013.01); *A61B 6/466* (2013.01); *A61B 6/467* (2013.01); *A61B 6/52* (2013.01); *A61B 6/5258* (2013.01); *A61B 6/58* (2013.01); *A61B 6/588* (2013.01); *A61B 6/589* (2013.01)

(58) Field of Classification Search
CPC ......... A61B 6/583; A61B 6/584; A61B 6/587; A61B 6/588; A61B 6/589

USPC ......... 375/62, 165, 189, 196–198, 205, 207, 375/209
See application file for complete search history.

(56) References Cited

U.S. PATENT DOCUMENTS

| | | | | |
|---|---|---|---|---|
| 7,492,864 | B2 * | 2/2009 | Peeters ................. | A61B 6/542 378/165 |
| 7,720,198 | B2 * | 5/2010 | Schliermann .......... | A61B 6/542 378/108 |
| 10,542,958 | B2 * | 1/2020 | Merckx ................. | A61B 6/469 |
| 10,846,853 | B2 * | 11/2020 | Ihara .................... | A61B 5/7264 |
| 12,080,001 | B2 * | 9/2024 | Ni .......................... | A61B 90/37 |
| 2008/0170657 | A1 | 7/2008 | Peeters | |
| 2017/0316562 | A1 | 11/2017 | Haberland et al. | |

* cited by examiner

VISUALIZATION OF TOUCH PANEL TO OBJECT DISTANCE IN X-RAY IMAGING

TECHNICAL FIELD

The present disclosure relates to the field of medical imaging technologies, and in particular, to a method and apparatus for visualization of a touch panel to object distance (TOD) in X-ray imaging.

BACKGROUND

X-rays are electromagnetic radiation with a wavelength between an ultraviolet light and a gamma ray. X-rays are penetrative and have different penetrating capacities for substances of different densities. In medicine, X-rays are generally used to project human organs and bones to form medical images.

An X-ray imaging system generally includes an X-ray generation assembly, a Bucky wall stand (BWS) assembly, an examination table assembly, a film holder assembly including a flat panel detector, a remote control host, and the like. The X-ray generation assembly emits, by using a high voltage provided by a high-voltage generator, X-rays that penetrate an irradiated imaging target and form medical image information of the imaging target on the flat panel detector. The flat panel detector sends the medical image information to the control host. The imaging target may stand near the BWS assembly or lie on the examination table assembly so as to receive X-ray photography of parts such as the head, chest, abdomen, and joints.

In an X-ray application program, a distance between a touch panel touched by a to-be-detected subject, including an object and the object, generally needs to be determined. For example, the object may be tissue, an organ, or a system of the to-be-detected subject. The touch panel to object distance (TOD) not only affects the quality of an X-ray image, but may also affect a dose. For example, in an application such as long bone splicing or free-mode dose control, a TOD indicator is particularly critical.

In a current practical application, a TOD is generally manually measured by staff using a ruler. A measurement value, for example, "A TOD is 10 cm", is displayed on a user interface of the control host. However, due to the lack of intuitive visualization processing, it is difficult for the staff to quickly and accurately understand the physical meaning of the value.

SUMMARY

Implementations of the present disclosure provide a method and apparatus for visualization of a touch panel to object distance (TOD) in X-ray imaging.

The technical solutions of the implementations of the present disclosure include:

A method for visualization of a TOD in X-ray imaging, including:
- obtaining a three-dimensional image of a to-be-detected subject that includes an object;
- determining a TOD;
- generating a first identifier at a position of a touch panel in the three-dimensional image; and
- generating a second identifier in the three-dimensional image, where a distance between the first identifier and the second identifier corresponds to the TOD.

It can be seen that, in this implementation of the present disclosure, the first identifier and the second identifier are generated in the three-dimensional image of the to-be-detected subject, and the TOD is intuitively displayed based on the distance between the first identifier and the second identifier, which helps quickly and accurately learn the TOD.

In an implementation, the generating a first identifier at a position of a touch panel in the three-dimensional image includes:
- determining a source-to-image distance (SID) and a touch panel-to-detector distance (TDD) based on an X-ray imaging protocol;
- determining the position of the touch panel in the three-dimensional image based on the SID and the TDD; and
- generating the first identifier in a predetermined three-dimensional shape at the position of the touch panel in the three-dimensional image.

Therefore, in this implementation of the present disclosure, the position of the touch panel in the three-dimensional image can be accurately determined by using a preset parameter corresponding to the X-ray imaging protocol. Furthermore, the first identifier in a three-dimensional shape is generated in this implementation of the present disclosure, thereby improving an identification effect.

In an implementation, the generating a first identifier at a position of a touch panel in the three-dimensional image includes:
- detecting the touch panel in the three-dimensional image in a target detection manner; and
- generating the first identifier in a predetermined three-dimensional shape at the position of the touch panel in the three-dimensional image.

It can be seen that, in this implementation of the present disclosure, the touch panel is directly detected from the three-dimensional image in a target detection manner, thereby quickly determining the position of the touch panel in the three-dimensional image. Furthermore, the first identifier in a three-dimensional shape is generated in this implementation of the present disclosure, thereby improving an identification effect.

In an implementation, the determining a TOD includes: determining a source-to-image distance (SID) and a touch panel-to-detector distance (TDD); determining, based on the three-dimensional image, a distance between a light source of a camera assembly and a predetermined key point located on a surface of the to-be-detected subject, where the predetermined key point corresponds to an X-ray imaging protocol; and determining the TOD based on the SID, the TDD, and the distance between the light source of the camera assembly and the predetermined key point.

Therefore, in this implementation of the present disclosure, the TOD can be automatically determined based on the three-dimensional image of the to-be-detected subject without manual measurement, thereby reducing the complexity and improving the accuracy.

In an implementation, the determining, based on the three-dimensional image, a distance between a light source of a camera assembly and a predetermined key point located on a surface of the to-be-detected subject includes:
- inputting the three-dimensional image into a key point recognition network;
- enabling the key point recognition network to recognize the predetermined key point located on the surface of the to-be-detected subject in the three-dimensional image; and
- determining, based on a distance measurement algorithm, the distance between the light source of the camera assembly and the recognized predetermined key point.

Therefore, in this implementation of the present disclosure, the predetermined key point is recognized through artificial intelligence, thereby greatly improving the processing efficiency.

In an implementation, an X-ray source coincides with the light source of the camera assembly; and the determining the TOD based on the SID, the TDD, and the distance between the light source of the camera assembly and the predetermined key point includes: determining the TOD, where TOD=$\gamma$*(SID−TDD−SOSD1), SID is the source to image distance, TDD is the touch panel to detector distance, SOSD1 is the distance between the light source of the camera assembly and the predetermined key point, and $\gamma$ is a correction factor: or an X-ray source does not coincide with the light source of the camera assembly; and the determining the TOD based on the SID, the TDD, and the distance between the light source of the camera assembly and the predetermined key point includes: determining a distance SOSD1 between the X-ray source and the predetermined key point based on the distance SOSD2 between the light source of the camera assembly and the predetermined key point; and determining the TOD, where TOD=$\gamma$*(SID−TDD−SOSD1), SID is the source to image distance, TDD is the touch panel to detector distance, and $\gamma$ is a correction factor.

It can be seen that when the X-ray source coincides with the light source of the camera assembly, the TOD is calculated in this implementation of the present disclosure. When the X-ray source does not coincide with the light source of the camera assembly, the TOD can also be calculated in this implementation of the present disclosure. In addition, the correction factor is introduced, thereby improving the calculation precision.

In an implementation, the method further includes:
receiving a user instruction; and
adjusting at least one of the following based on the user instruction:
a shape of the first identifier; a position of the first identifier: a shape of the second identifier; and a position of the second identifier.

Therefore, in this implementation of the present disclosure, the shape of the first identifier, the position of the first identifier, the shape of the second identifier, and the position of the second identifier in the three-dimensional image can be conveniently adjusted.

In an implementation, the method further includes:
determining a product of the TOD and a scale ratio of the three-dimensional image as the distance between the first identifier and the second identifier.

It can be learned that the distance between the first identifier and the second identifier in the three-dimensional image can be quickly determined by multiplying the TOD by the scale ratio of the three-dimensional image.

An apparatus for visualization of a TOD in X-ray imaging is provided, including:
an obtaining module, configured to obtain a three-dimensional image of a to-be-detected subject that includes an object;
a determining module, configured to determine a TOD;
a first generation module, configured to generate a first identifier at a position of a touch panel in the three-dimensional image; and
a second generation module, configured to generate a second identifier in the three-dimensional image, where a distance between the first identifier and the second identifier corresponds to the TOD.

It can be seen that, in this implementation of the present disclosure, the first identifier and the second identifier are generated in the three-dimensional image of the object, and the TOD is intuitively displayed based on the distance between the first identifier and the second identifier, which helps quickly and accurately learn the TOD.

In an implementation, the first generation module is configured to determine a SID and a TDD based on an X-ray imaging protocol: determine the position of the touch panel in the three-dimensional image based on the SID and the TDD; and generate the first identifier in a predetermined three-dimensional shape at the position of the touch panel in the three-dimensional image.

Therefore, in this implementation of the present disclosure, the position of the touch panel in the three-dimensional image can be accurately determined by using a preset parameter corresponding to the X-ray imaging protocol. Furthermore, the first identifier in a three-dimensional shape is generated in this implementation of the present disclosure, thereby improving an identification effect.

In an implementation, the first generation module is configured to detect the touch panel in the three-dimensional image in a target detection manner; and generate the first identifier in a predetermined three-dimensional shape at the position of the touch panel in the three-dimensional image.

It can be seen that, in this implementation of the present disclosure, the touch panel is directly detected from the three-dimensional image in a target detection manner, thereby quickly determining the position of the touch panel in the three-dimensional image. Furthermore, the first identifier in a three-dimensional shape is generated in this implementation of the present disclosure, thereby improving an identification effect.

In an implementation, the determining module is configured to determine a SID and a TDD; determine, based on the three-dimensional image, a distance between a light source of a camera assembly and a predetermined key point located on a surface of the to-be-detected subject, where the predetermined key point corresponds to an X-ray imaging protocol; and determine the TOD based on the SID, the TDD, and the distance between the light source of the camera assembly and the predetermined key point.

Therefore, in this implementation of the present disclosure, the TOD can be automatically determined based on the three-dimensional image of the to-be-detected subject without manual measurement, thereby reducing the complexity.

In an implementation, the determining module is configured to input the three-dimensional image into a key point recognition network: enable the key point recognition network to recognize the predetermined key point located on the surface of the to-be-detected subject in the three-dimensional image; and determine, based on a distance measurement algorithm, the distance between the light source of the camera assembly and the recognized predetermined key point.

Therefore, in this implementation of the present disclosure, the predetermined key point is recognized through artificial intelligence, thereby greatly improving the processing efficiency.

In an implementation, an X-ray source coincides with the light source of the camera assembly; and the determining module is configured to determine the TOD, where TOD=$\gamma$* (SID−TDD−SOSD1), SID is the source to image distance, TDD is the touch panel to detector distance, SOSD1 is the distance between the light source of the camera assembly and the predetermined key point, and $\gamma$ is a correction factor: or an X-ray source does not coincide with the light source of the camera assembly; and the determining module is configured to determine a distance SOSD1 between the X-ray source and the predetermined key point based on the distance SOSD2 between the light source of the camera assembly and the predetermined key point; and determine the TOD, where TOD=γ*(SID−TDD−SOSD1), SID is the source to image distance, TDD is the touch panel to detector distance, and γ is a correction factor.

It can be seen that when the X-ray source coincides with the light source of the camera assembly, the TOD is calculated in this implementation of the present disclosure. When the X-ray source does not coincide with the light source of the camera assembly, the TOD can also be calculated in this implementation of the present disclosure. In addition, the correction factor is introduced, thereby improving the calculation precision.

In an implementation, the apparatus further includes:
an adjustment module, configured to receive a user instruction; and adjust at least one of the following based on the user instruction:
a shape of the first identifier: a position of the first identifier; a shape of the second identifier; and a position of the second identifier.

Therefore, in this implementation of the present disclosure, the shape of the first identifier, the position of the first identifier, the shape of the second identifier, and the position of the second identifier in the three-dimensional image can be conveniently adjusted.

In an implementation, the second generation module is further configured to determine a product of the TOD and a scale ratio of the three-dimensional image as the distance between the first identifier and the second identifier.

It can be learned that, the distance between the first identifier and the second identifier in the three-dimensional image can be quickly determined by multiplying the TOD by the scale ratio of the three-dimensional image.

An apparatus for visualization of a TOD in X-ray imaging is provided, including a processor and a memory, where the memory stores an application program executable by the processor, and the application program is configured to enable the processor to perform any one of the foregoing methods for visualization of a TOD in X-ray imaging.

It can be seen that this implementation of the present disclosure provides an apparatus with a processor-memory architecture. A first identifier and a second identifier are generated in a three-dimensional image of a to-be-detected subject, and a TOD is intuitively displayed based on a distance between the first identifier and the second identifier, which helps quickly and accurately learn the TOD.

A computer-readable storage medium is provided, storing computer-readable instructions, the computer-readable instructions being used to perform any one of the foregoing methods for visualization of a TOD in X-ray imaging.

Therefore, this implementation of the present disclosure provides a computer-readable storage medium including computer-readable instructions. A first identifier and a second identifier are generated in a three-dimensional image of a to-be-detected subject, and a TOD is intuitively displayed based on a distance between the first identifier and the second identifier, which helps quickly and accurately learn the TOD.

REFERENCE NUMERALS ARE AS FOLLOWS

Figure 1:
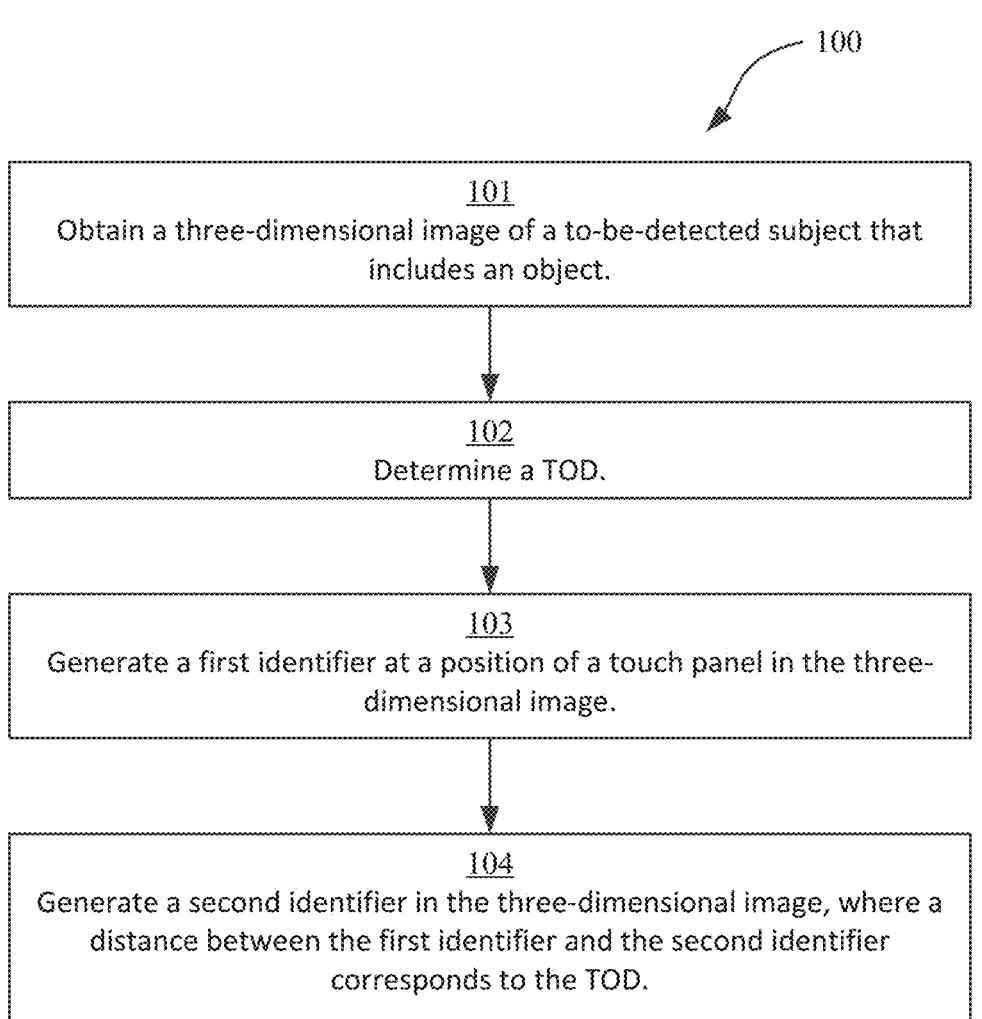
FIG. 1 is a flowchart of a method for visualization of a TOD in X-ray imaging according to an implementation of the present disclosure.

100 Method for visualization of a TOD
101~104 Step
201, 301, 401 Touch panel
202, 302, 402 Object
70 Ceiling
71 X-ray bulb tube
72 Beam limiting device
73 Three-dimensional camera
75 To-be-detected subject
76 Examination table assembly
77 Floor
78 Film holder assembly
79 Telescope tube sleeve
81/82 Installation position
83 Vertical column
90 Flat panel detector
91 Panel of film holder assembly
92 Neck reference line
93 Abdominal reference line
95 Spine reference line
98 Supporting plate
60 Control host
600 Apparatus for visualization of a TOD
601 Obtaining module
602 Determining module
603 First generation module
604 Second generation module
605 Adjustment module
700 Apparatus for visualization of a TOD
701 Processor
702 Memory

DETAILED DESCRIPTION

To make technical solutions and advantages of the present disclosure clearer and more understandable, the present disclosure is further described in detail below with reference to the accompanying drawings and implementations. It should be understood that the specific implementations described herein are merely used to illustratively explain the present disclosure but are not intended to limit the protection scope of the present disclosure.

For brief and intuitive descriptions, the following describes the solutions of the present disclosure by describing several representative implementations. A great quantity of details of the implementations is only used to help understand the solutions of the present disclosure. However, obviously, implementation of the technical solutions of the present disclosure may not be limited to such details. To avoid unnecessary ambiguity in the solutions of the present disclosure, some implementations are not described in detail, but only a framework is given. In the following, "include" refers to "include, but is not limited to," and "according to . . . " refers to "at least according to . . . , but not limited to only according to . . . ". Because of Chinese language habits, the following does not particularly specify the quantity of a component, which means that the component may be one or more or can be understood as at least one.

Taking into account a defect that a measurement value of a touch panel to object distance (TOD) fails to be directly displayed in the prior art, the implementations of the present disclosure provide a technical solution for visualization of a TOD in X-ray imaging. In the implementations of the present disclosure, a first identifier is generated at a position of a touch panel in a three-dimensional image of a to-be-detected subject, and a second identifier is correspondingly generated in the three-dimensional image based on a distance between the touch panel and an object located inside the to-be-detected subject, so that a staff visually perceives a distance between the first identifier and the second identifier, and can intuitively, quickly, and accurately learn a TOD.

FIG. 1 is a flowchart of a method for visualization of a TOD in X-ray imaging according to an implementation of the present disclosure. Preferably, the method shown in FIG. 1 may be performed by a controller. The controller may be implemented as or integrated into a control host in an X-ray imaging system or may be implemented as a control unit independent of the control host.

As shown in FIG. 1, the method includes the following steps.

Step 101: Obtain a three-dimensional image of a to-be-detected subject that includes an object.

Herein, the to-be-detected subject is a living thing or a non-living thing on which X-ray imaging needs to be performed. The to-be-detected subject includes the object, and the object is generally located inside the to-be-detected subject. For example, when the to-be-detected subject is a living thing, the object may be tissue, an organ, a system, or the like of the living thing. The object generally corresponds to a specific X-ray imaging protocol. For example, for a whole spine scan protocol, the object is the spine of the to-be-detected subject.

In an implementation, in step 101, a camera assembly may be used to photograph the to-be-detected subject to obtain the three-dimensional image of the to-be-detected subject. In another implementation, in step 101, the three-dimensional image of the to-be-detected subject may be obtained from a storage medium (for example, a cloud or a local database). The three-dimensional image is obtained by using a camera assembly to photograph the to-be-detected subject.

Herein, a light source of the camera assembly may coincide with an X-ray source in an X-ray imaging system or may not coincide with the X-ray source.

When the light source of the camera assembly coincides with the X-ray source in the X-ray imaging system, the camera assembly is generally fixed on an encloser of a bulb tube or a housing of a beam limiting device of an X-ray generation assembly. For example, a groove for accommodating the camera assembly is arranged on the encloser of the bulb tube or the housing of the beam limiting device, and the camera assembly is fixed to the groove by means of a bolted connection, buckle connection, a wire rope sleeve, or the like.

When the light source of the camera assembly does not coincide with the X-ray source in the X-ray imaging system, the camera assembly may be arranged in an examination room in which the to-be-detected subject is located or at any position suitable for photographing the to-be-detected subject, for example, on the ceiling, floor, various components in a medical imaging system, or the like.

In an implementation, the camera assembly includes at least one three-dimensional camera. The three-dimensional camera photographs the to-be-detected subject by using three-dimensional imaging technologies to generate the three-dimensional image of the to-be-detected subject.

In an implementation, the camera assembly includes at least two two-dimensional cameras. The two-dimensional cameras are respectively arranged at predetermined positions. In practice, a person skilled in the art may select suitable positions as the predetermined positions according to requirements to arrange the two-dimensional cameras. The camera assembly may further include an image processor. The image processor combines two-dimensional images captured by the two-dimensional cameras into the three-dimensional image of the to-be-detected subject. The depth of field used by the image processor in the combination may be the depth of field of any two-dimensional image. Optionally, each of the two-dimensional cameras may send a two-dimensional image captured by the two-dimensional camera to an image processor outside the camera assembly so that the image processor outside the camera assembly can combine two-dimensional images captured by the two-dimensional cameras into the three-dimensional image of the to-be-detected subject. The depth of field used by the image processor outside the camera assembly in a combination process may also be the depth of field of any two-dimensional image. Specifically, the image processor outside the camera assembly may be implemented as a control host in the X-ray imaging system or may be implemented as an independent control unit separate from the X-ray imaging system. Each of the two-dimensional cameras may be arranged in the examination room in which the to-be-detected subject is located or at any position suitable for photographing the to-be-detected subject, for example, on the ceiling, floor, various components in the X-ray imaging system, or the like.

In an implementation, the camera assembly may include at least one two-dimensional camera and at least one depth-of-field sensor. The at least one two-dimensional camera and the at least one depth of field sensor are mounted at the same position. The camera assembly may further include an image processor. The image processor generates the three-dimensional image of the to-be-detected subject by using both a depth of field provided by the depth of field sensor and a two-dimensional image provided by the two-dimensional camera. Optionally, the two-dimensional camera sends a captured two-dimensional image of the to-be-detected subject to an image processor outside the camera assembly, and the depth of field sensor sends an acquired depth of field to the image processor outside the camera assembly so that the image processor outside the camera assembly generates the three-dimensional image of the to-be-detected subject by using both the depth of field and the two-dimensional image. Preferably, the image processor outside the camera assembly may be implemented as a control host in the X-ray imaging system or may be implemented as an independent control unit separate from the X-ray imaging system. The two-dimensional camera may be arranged in the examination room in which the to-be-detected subject is located or at any position suitable for photographing the to-be-detected subject, for example, on the ceiling, floor, various components in a medicine imaging system, or the like.

After acquiring the three-dimensional image of the to-be-detected subject, the camera assembly may send, by using a wired interface or a wireless interface, the three-dimensional image to the controller that performs the process in FIG. 1. Preferably, the wired interface includes at least one of the following: a universal serial bus interface, a controller area network interface, a serial port, or the like. The wireless interface includes at least one of the following: an infrared interface, a near-field communication interface, a Bluetooth interface, a ZigBee interface, a wireless broadband interface, or the like.

The foregoing exemplarily describes a typical example in which the camera assembly photographs the to-be-detected subject to generate a three-dimensional image. A person skilled in the art may realize that the description is only exemplary and is not used to limit the protection scope of the implementations of the present disclosure.

Step 102: Determine a TOD.

Herein, a touch panel is a panel touched by the to-be-detected subject in an X-ray application. The touch panel may isolate the to-be-detected subject from an imaging plane. The touch panel generally has the following meanings:

(1) When the X-ray imaging system works in an examination table mode, the touch panel is a bed board of an examination table.

(2) When the X-ray imaging system works in a Bucky wall stand (BWS) mode under a whole spine imaging protocol, the touch panel is a supporting plate used to assist the to-be-detected subject to stand.

(3) When the X-ray imaging system works in a BWS mode under a non-whole spine imaging protocol (for example, a chest imaging protocol or a knee imaging protocol), the touch panel is a panel of a film holder assembly, and a flat panel detector is inserted into the film holder assembly.

(4). When the X-ray imaging system works in a free exposure mode (that is, the to-be-detected subject directly touches the flat panel detector), the touch panel is a panel of the flat panel detector touched by the to-be-detected subject.

In an implementation, the TOD can be manually measured by a staff using a ruler.

Taking into account many defects in manual measurement of a TOD by using a ruler, the implementations of the present disclosure further provide a technical solution for automatically determining a TOD. In this implementation of the present disclosure, the TOD can be automatically determined based on the three-dimensional image of the imaging object, thereby reducing the cumbersome workload of manual measurement of the TOD.

In an implementation, in step 102, the determining a TOD includes: determining a source-to-image distance (SID) and a touch panel-to-detector distance (TDD): determining, based on the three-dimensional image, a distance between a light source of a camera assembly and a predetermined key point located on a surface of the to-be-detected subject, where the predetermined key point corresponds to an X-ray imaging protocol; and determining the TOD based on the SID, the TDD, and the distance between the light source of the camera assembly and the predetermined key point. Herein, an imaging plane is a plane on which an X-ray image is formed. The imaging plane can be determined based on a position of an imaging medium in a detector. The detector is an X-ray detector and is generally a flat panel detector.

Both the SID and the TDD correspond to the X-ray imaging protocol. After the X-ray imaging protocol is determined, both the SID and the TDD are known values. Therefore, the controller that performs the process in FIG. 1 can determine the SID and the TDD based on the determined X-ray imaging protocol. Herein, the predetermined key point is a feature point that corresponds to the X-ray imaging protocol and is on the surface of the to-be-detected subject. Depending on different X-ray imaging protocols, the predetermined key point may be the left shoulder, the right shoulder, the left knee, the right knee, the left ear, the right ear, the left rump, the right rump, or the like of the to-be-detected subject. For example, when the X-ray imaging protocol is implemented as a whole spine imaging protocol, the predetermined key point may be the left shoulder or the right shoulder. When the X-ray imaging protocol is implemented as a knee imaging protocol, the predetermined key point may be the left knee or the right knee, and so on. The predetermined key point located on the surface of the to-be-detected subject in the three-dimensional image may be recognized by using a feature point extraction algorithm such as a scale-invariant feature transform (SIFT) algorithm, a speeded-up robust feature (SURF) algorithm, or an oriented fast and rotated brief (ORB) algorithm. Preferably, the predetermined key point located on the surface of the to-be-detected subject in the three-dimensional image is automatically recognized through artificial intelligence, so that the artificial intelligence technologies are introduced into a medical image generation process to improve the efficiency of key point recognition.

In an implementation, the determining, based on the three-dimensional image, a distance between a light source of a camera assembly and a predetermined key point located on a surface of the to-be-detected subject specifically includes: inputting the three-dimensional image into a key point recognition network: enabling the key point recognition network to recognize the predetermined key point located on the surface of the to-be-detected subject in the three-dimensional image; and determining, based on a distance measurement algorithm (for example, various three-dimensional positioning algorithms), the distance between the light source of the camera assembly and the recognized predetermined key point.

In an implementation, the method further includes a process of generating the key point recognition network. The process specifically includes: obtaining training data of the key point recognition network; and training a preset neural network model by using the training data, where when an accuracy rate of an output result of the neural network model is greater than a predetermined threshold, the key point recognition network is obtained. Specifically, the neural network model may be implemented as a feedforward neural network model, a radial basis function neural network model, a long short-term memory (LSTM) network model, an echo state network (ESN), a gate recurrent unit (GRU) network model, a deep residual network model, or the like.

The foregoing exemplarily describes a typical embodiment of a neural network model. A person skilled in the art may realize that the description is only exemplary and is not used to limit the protection scope of the implementations of the present disclosure.

In an implementation, when the X-ray source coincides with the light source of the camera assembly, the determining the TOD based on the SID, the TDD, and the distance between the light source of the camera assembly and the predetermined key point specifically includes: determining the TOD, where $TOD=\gamma*(SID-TDD-SOSD1)$, SID is the source to image distance, TDD is the touch panel to detector distance, SOSD1 is the distance between the light source of the camera assembly and the predetermined key point, and $\gamma$ is a correction factor. In this case, because the X-ray source coincides with the light source of the camera assembly, SOSD1 is also a distance between the X-ray source and the predetermined key point.

In an implementation, when the X-ray source does not coincide with the light source of the camera assembly, the determining the TOD based on the SID, the TDD, and the distance between the light source of the camera assembly and the predetermined key point specifically includes: determining a distance SOSD1 between the X-ray source and the predetermined key point based on the distance SOSD2 between the light source of the camera assembly and the predetermined key point; and determining the TOD, where $TOD=\gamma*(SID-TDD-SOSD1)$, SID is the source to image distance, TDD is the touch panel to detector distance, and $\gamma$ is a correction factor. Specifically, the determining a distance SOSD1 between the X-ray source and the predetermined key point based on the distance SOSD2 between the light source of the camera assembly and the predetermined key point includes: determining a transformation matrix from a coordinate system of the camera assembly to a coordinate system of the X-ray generation assembly: determining three-dimensional coordinates of the predetermined key point in the coordinate system of the camera assembly based on the distance SOSD2 between the light source of the camera assembly and the predetermined key point; determining three-dimensional coordinates of the predetermined key point in the coordinate system of the X-ray generation assembly based on the three-dimensional coordinates of the predetermined key point in the coordinate system of the camera assembly and the transformation matrix; and determining the distance SOSD1 between the X-ray source and the predetermined key point based on the three-dimensional coordinates of the predetermined key point in the coordinate system of the X-ray generation assembly.

Considering that the to-be-detected subject generally has a thickness, the TOD is further corrected by using the correction factor in this implementation of the present disclosure In an implementation, the correction factor may be provided by a user based on the experience of the user. In another implementation, the three-dimensional image may be inputted into a correction factor determining network corresponding to the X-ray imaging protocol, to determine the correction factor by the correction factor determining network. The method 100 further includes a process of generating the correction factor determining network. The process specifically includes the following steps: labeling respective correction factors for historical three-dimensional images as training data; and training a neural network model by using the labeled historical three-dimensional images, where when an accuracy rate of an output result of the neural network model is greater than a predetermined threshold, the correction factor determining network is obtained. Specifically, the neural network model may be implemented as a feedforward neural network model, a radial basis function neural network model, an LSTM network model, an ESN, a GRU network model, a deep residual network model, or the like.

Step 103: Generate a first identifier at a position of a touch panel in the three-dimensional image.

In an implementation, the generating a first identifier at a position of a touch panel in the three-dimensional image includes: determining a SID and a TDD based on an X-ray imaging protocol: determining the position of the touch panel in the three-dimensional image based on the SID and the TDD; and generating the first identifier in a predetermined three-dimensional shape at the position of the touch panel in the three-dimensional image.

For example, a distance between the X-ray source and the touch panel is obtained by subtracting the TDD from the SID. Next, a coordinate range of the touch panel in a real-world coordinate system is determined by using the distance between the X-ray source and the touch panel. The coordinate range is multiplied by a scale ratio of the three-dimensional image (a dimension ratio of the to-be-detected subject in the three-dimensional image to the photographed to-be-detected subject in the real world) so that a coordinate range of the touch panel in the three-dimensional image, that is, the position of the touch panel in the three-dimensional image, can be obtained.

In an implementation, the generating a first identifier at a position of a touch panel in the three-dimensional image includes: detecting the touch panel in the three-dimensional image in a target detection manner; and generating the first identifier in a predetermined three-dimensional shape at the position of the touch panel in the three-dimensional image.

For example, the target detection manner may include: a target detection framework algorithm that is represented by a region-based convolutional neural network (R-CNN), an end-to-end target detection framework algorithm that is represented by you only look once (YOLO) and converts target detection into a regression problem, or the like.

The first identifier may be any three-dimensional shape such as a cuboid, a cube, or a sphere, and is preferably implemented as a cuboid.

Step 104: Generate a second identifier in the three-dimensional image, where a distance between the first identifier and the second identifier corresponds to the TOD.

Herein, the second identifier is used to identify the object. The second identifier may be any three-dimensional shape such as a cuboid, a cube, or a sphere, and is preferably implemented as a cuboid. In an implementation, a product of the TOD and the scale ratio of the three-dimensional image is determined as the distance between the first identifier and the second identifier.

It can be seen that, in this implementation of the present disclosure, the first identifier and the second identifier are generated in the three-dimensional image of the object, and the TOD is intuitively displayed based on the distance between the first identifier and the second identifier, which helps quickly and accurately learn the TOD.

In an implementation, the method further includes: receiving a user instruction; and adjusting at least one of the following based on the user instruction: a shape of the first identifier; a position of the first identifier: a shape of the second identifier; and a position of the second identifier. Therefore, the TOD can be conveniently adjusted by directly adjusting properties related to the first identifier and the second identifier in the three-dimensional image. For example, when a user finds that an automatically detected TOD is too small, the user may trigger, by using a peripheral device (such as a mouse), an instruction to manually adjust a position of the first identifier, thereby increasing the TOD.

Figure 2A:
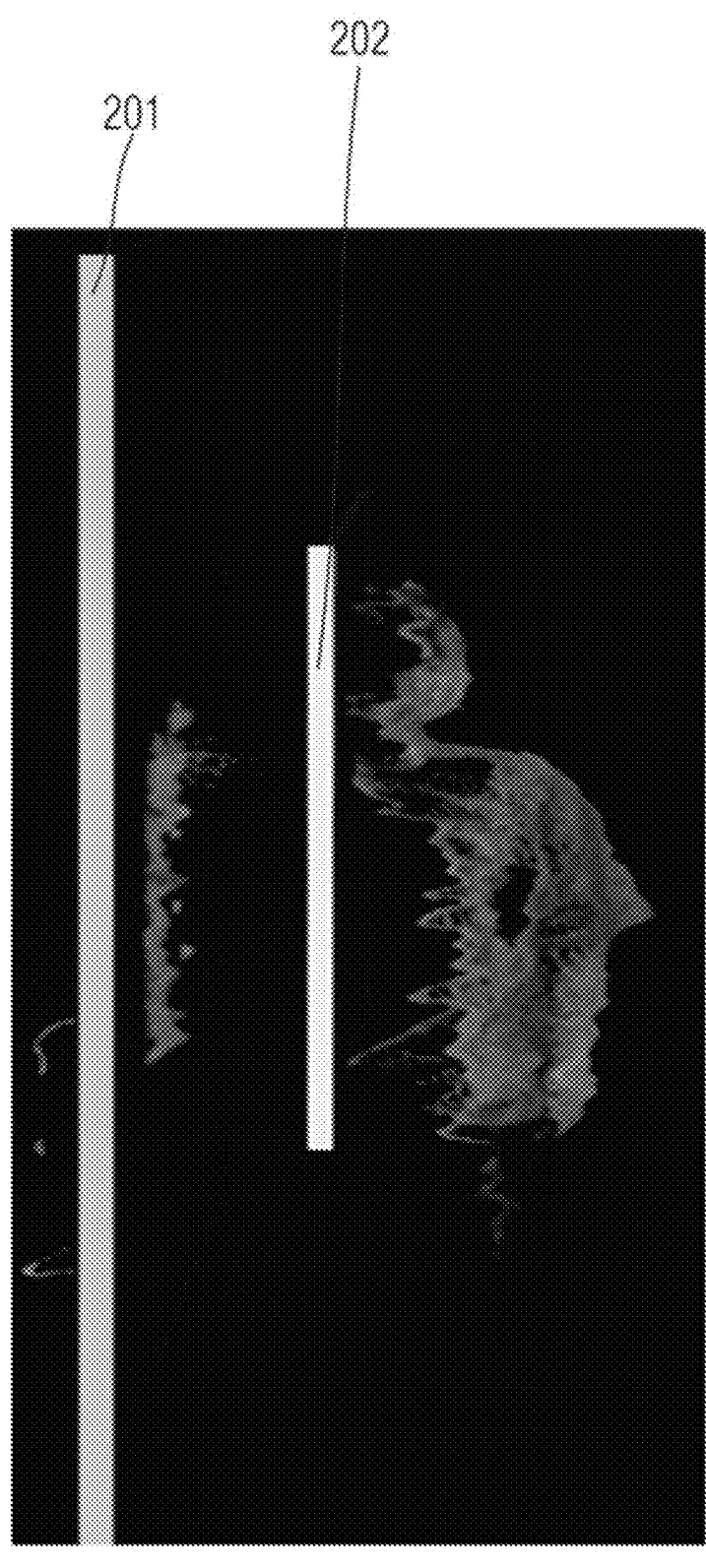
FIG. 2A is a first schematic diagram of an example of visualization of a TOD according to an implementation of the present disclosure.

FIG. 2A is a first schematic diagram of an example of visualization of a TOD according to an implementation of the present disclosure.

In FIG. 2A, a whole spine imaging protocol is used. An object is the spine of a to-be-detected subject. The left shoulder of the to-be-detected subject is against a touch panel, and an X-ray bulb tube faces toward the right shoulder of the to-be-detected subject. A three-dimensional image of the to-be-detected subject includes a first identifier 201 used to identify the touch panel and a second identifier 202 used to identify a spine reference line. Both the first identifier 201 and the second identifier 202 are cuboids.

Figure 2B:
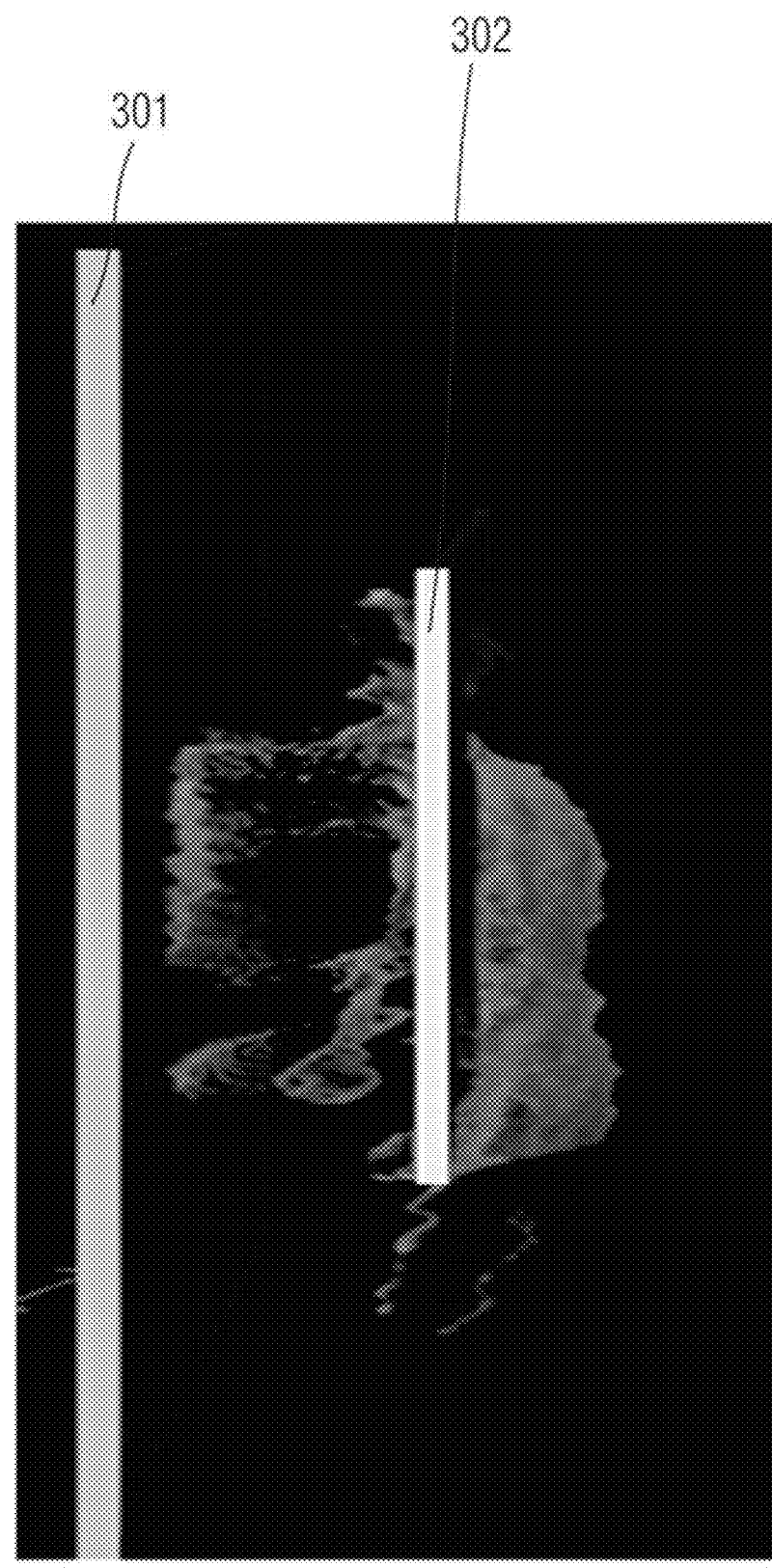
FIG. 2B is a second schematic diagram of an example of visualization of a TOD according to an implementation of the present disclosure.

FIG. 2B is a second schematic diagram of an example of visualization of a TOD according to an implementation of the present disclosure.

In FIG. 2B, a whole spine imaging protocol is used. An object is the spine of a to-be-detected subject. The face of the to-be-detected subject faces towards a touch panel, and an X-ray bulb tube faces towards the back of the to-be-detected subject. A three-dimensional image of the to-be-detected subject includes a first identifier 301 used to identify the touch panel and a second identifier 302 used to identify a spine reference line. Both the first identifier 301 and the second identifier 302 are cuboids.

Figure 2C:
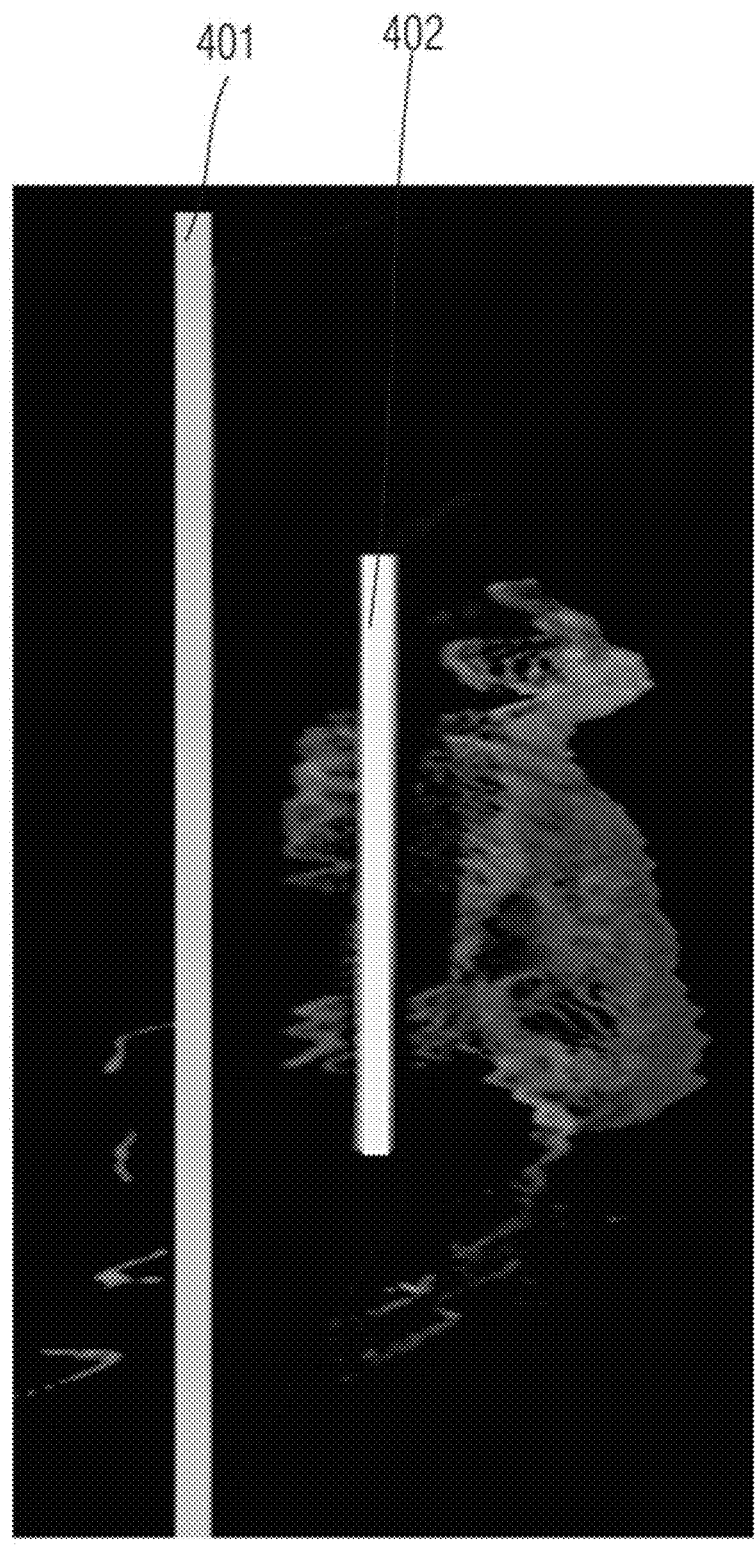
FIG. 2C is a third schematic diagram of an example of visualization of a TOD according to an implementation of the present disclosure.

FIG. 2C is a third schematic diagram of an example of visualization of a TOD according to an implementation of the present disclosure.

In FIG. 2C, a whole spine imaging protocol is used. An object is the spine of a to-be-detected subject. The back of the to-be-detected subject is against a touch panel, and an X-ray bulb tube faces towards the face of the to-be-detected subject. A three-dimensional image of the to-be-detected subject includes a first identifier 401 used to identify the touch panel and a second identifier 402 used to identify a spine reference line. Both the first identifier 401 and the second identifier 402 are cuboids.

In FIG. 2A to FIG. 2C, a typical example of visualization of a TOD is described by using a setup in a whole spine imaging protocol as an example. A person skilled in the art may realize that the description is only exemplary and is not used to limit the protection scope of the implementations of the present disclosure.

An exemplary process of determining a TOD is described below in detail with reference to the accompanying drawings.

Figure 3:
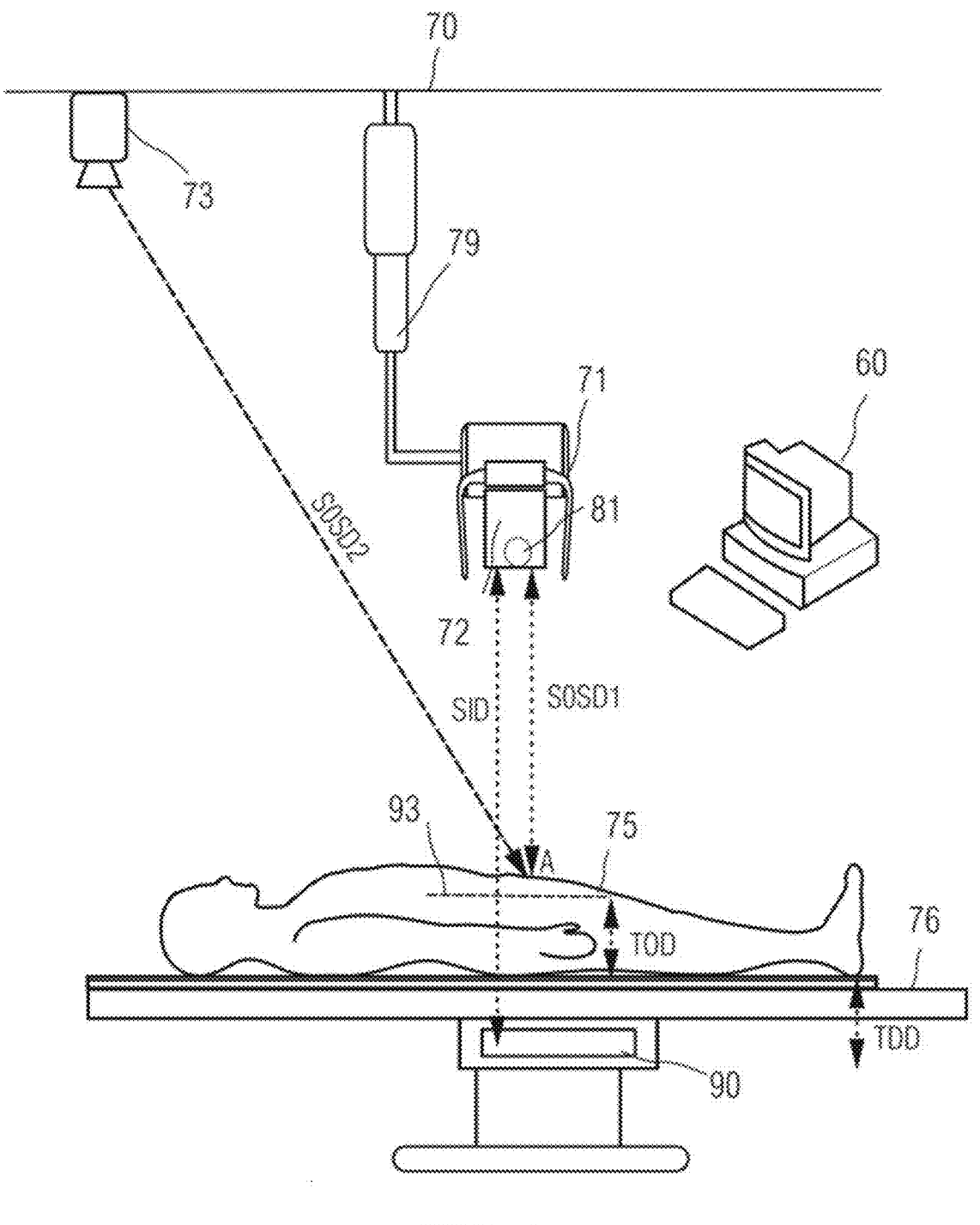
FIG. 3 is a schematic diagram of an example of determining a TOD in an examination table mode according to an implementation of the present disclosure.

FIG. 3 is a schematic diagram of an example of determining a TOD in an examination table mode according to an implementation of the present disclosure.

In FIG. 3, an X-ray generation assembly including an X-ray tube 71 and a beam limiting device 72 is connected to a telescope tube sleeve 79 by using a supporting piece. The telescope tube sleeve 79 is connected to a ceiling 70. Furthermore, a three-dimensional camera 73 is fixed on the ceiling 70. A photographing direction of the three-dimensional camera 73 faces towards a to-be-detected subject 75 on an examination table assembly 76. The examination table assembly 76 is further provided with a flat panel detector 90. A control host 60 may be a control host disposed in a local control room or may be a remote control host such as a control host in a cloud.

The control host 60 includes a trained key point recognition network and a trained correction factor determining network. A training process of the key point recognition network includes: establishing an artificial neural network model: inputting labeled three-dimensional images as training data into the artificial neural network model; and training the artificial neural network model as the key point recognition network. The method for obtaining the training data for training the key point recognition network may include: first capturing a large quantity of three-dimensional images about an imaging target (for example, various people) by using a three-dimensional camera arranged at a preset position. Furthermore, experts mark the three-dimensional images to recognize key points. A training process of the correction factor determining network includes: establishing an artificial neural network model: inputting labeled three-dimensional images as training data into the artificial neural network model; and training the artificial neural network model as the correction factor determining network. The method for obtaining the training data for training the correction factor determining network may include: first capturing a large quantity of three-dimensional images about an imaging target (for example, various people) by using a three-dimensional camera arranged at a preset position. Furthermore, experts mark correction factors on the three-dimensional images based on experience.

A supervised learning manner may be used in the training processes of the correction factor determining network and the key point recognition network. Parameters of the artificial neural network model can be adjusted by using an optimization method (for example, stochastic gradient descent) so that an error between a prediction result of the artificial neural network model and a labeling result keeps decreasing until the error converges.

Assuming that an X-ray imaging protocol is an abdominal imaging protocol, the three-dimensional camera 73 photographs the to-be-detected subject 75 to acquire a three-dimensional image of the to-be-detected subject 75. The three-dimensional camera 73 sends the three-dimensional image of the to-be-detected subject 75 to the control host 60 through wired or wireless communication with the control host 60. The control host 60 determines that a predetermined key point corresponding to the abdominal imaging protocol is the belly button.

The key point recognition network in the control host 60 recognizes a belly button point A located on a surface of the to-be-detected subject 75 in the three-dimensional image of the to-be-detected subject 75. The control host 60 determines a distance SOSD2 between a light source of the three-dimensional camera 73 and the recognized belly button point A by using a distance measurement algorithm and determines three-dimensional coordinates of the belly button point A in a coordinate system of the three-dimensional camera 73 based on the SOSD2. The control host 60 determines three-dimensional coordinates of the belly button point A in a coordinate system of the X-ray generation assembly based on the three-dimensional coordinates of the belly button point A in the coordinate system of the three-dimensional camera 73 and based on a transformation matrix between the coordinate system of the three-dimensional camera 73 and the coordinate system of the X-ray generation assembly. The control host 60 then determines a distance SOSD1 between the X-ray source and the belly button point A by using the three-dimensional coordinates of the belly button point A in the coordinate system of the X-ray generation assembly.

The control host 60 stores preset parameters of the abdominal imaging protocol. The preset parameters include a SID and a TDD. Herein, a distance between the X-ray source and an imaging plane of the flat panel detector 90 is the SID, and a distance between a bed board 76 (that is, a touch panel) and the flat panel detector 90 is the TDD. The correction factor determining network in the control host 60 determines a correction factor $\gamma$ of the three-dimensional image of the to-be-detected subject 75. A TOD is a distance between an abdominal reference line 93 (that is, the object) of the to-be-detected subject 75 and the bed board 76 (that is, the touch panel). The control host 60 calculates the TOD, where TOD=$\gamma$*(SID–TDD–SOSD1).

The three-dimensional camera 73 may not be arranged on the ceiling 70. For example, the three-dimensional camera 73 may be arranged at an installation position 81 on a housing of the beam limiting device 72, to help the X-ray source coincide with the light source of the three-dimensional camera 73.

When the X-ray source coincides with the light source of the three-dimensional camera 73, the control host 60 calculates the TOD, where TOD=$\gamma$ *(SID–TDD–SOSD1). In this case, the control host 60 determines the distance SOSD1 between the light source of the three-dimensional camera 73 and the recognized belly button point A by using the distance measurement algorithm. SOSD1 is also the distance between the X-ray source and the belly button point A.

The bed board 76 can be detected in a target detection manner in the three-dimensional image captured by the three-dimensional camera 73. A first identifier in a predetermined three-dimensional shape is generated at a position of the bed board 76 in the three-dimensional image. Furthermore, a second identifier is generated in a region in which the to-be-detected subject 75 is located in the three-dimensional image. A distance between the first identifier and the second identifier is a product of a calculated TOD and a scale ratio of the three-dimensional image.

Therefore, a distance between the bed board 76 and the abdominal reference line 93 can be intuitively displayed by displaying the three-dimensional image including the first identifier and the second identifier.

Figure 4:
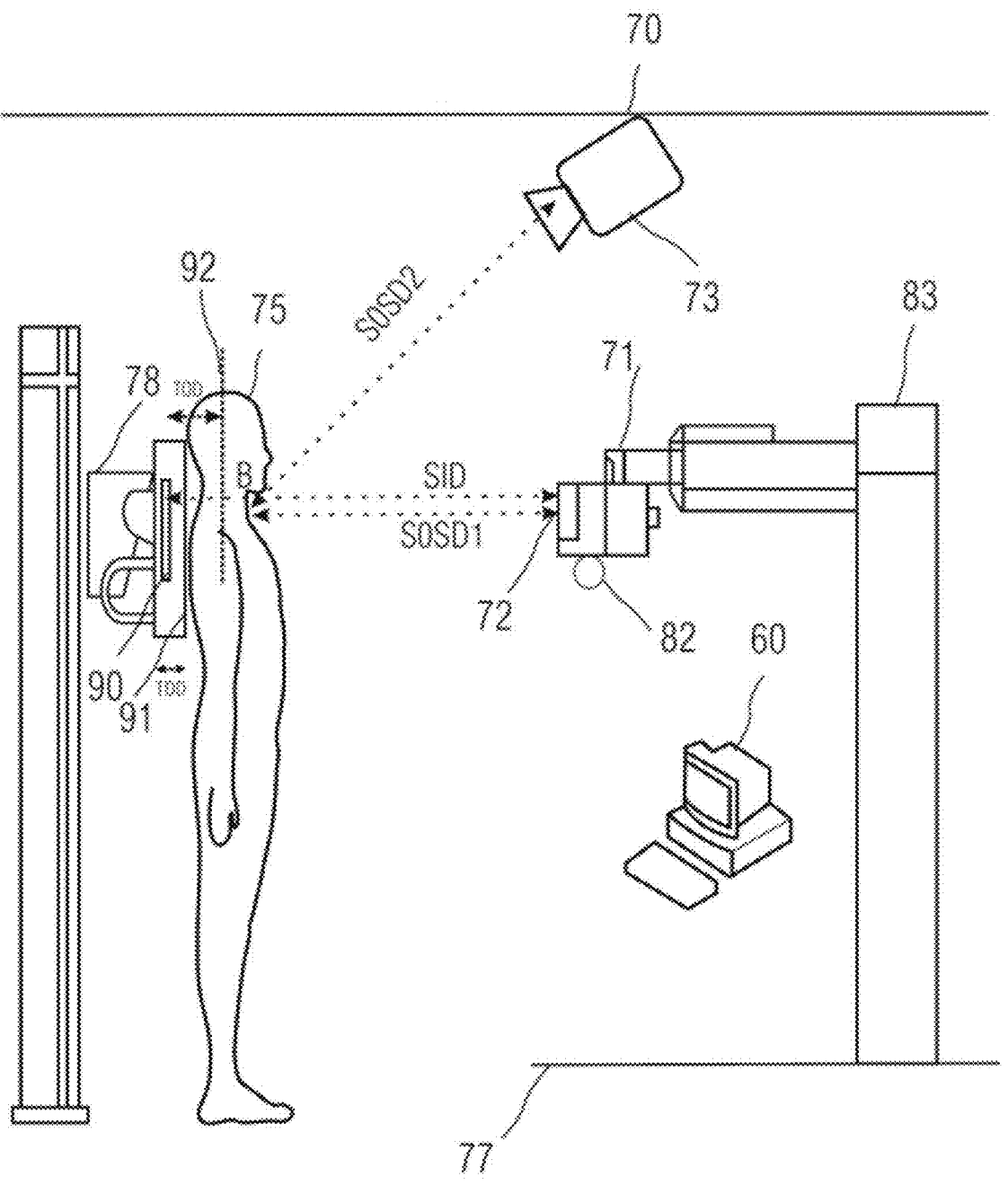
FIG. 4 is a schematic diagram of an example of determining a TOD in a BWS mode (non-whole spine scan) according to an implementation of the present disclosure.

FIG. 4 is a schematic diagram of an example of determining a TOD in a BWS mode (non-whole spine scan) according to an implementation of the present disclosure.

In FIG. 4, an X-ray generation assembly including an X-ray tube 71 and a beam limiting device 72 is connected, by using a supporting piece, to a vertical column 83 arranged on a floor 77. A to-be-detected subject 75 stands near a film holder assembly 78. Furthermore, a three-dimensional camera 73 is fixed on a ceiling 70. A photographing direction of the three-dimensional camera 73 faces towards the to-be-detected subject 75 near the film holder assembly 78. The film holder assembly 78 is further provided with a flat panel detector 90.

A control host 60 may be a control host disposed in a local control room or may be a remote control host such as a control host in a cloud.

The control host 60 includes a trained key point recognition network and a trained correction factor determining network. A training process of the key point recognition network includes: establishing an artificial neural network model: inputting labeled three-dimensional images as training data into the artificial neural network model; and training the artificial neural network model as the key point recognition network. The method for obtaining the training data for training the key point recognition network may include: first capturing a large quantity of three-dimensional images about an imaging target (for example, various people) by using a three-dimensional camera arranged at a preset position. Furthermore, experts mark the three-dimensional images to recognize key points. A training process of the correction factor determining network includes: establishing an artificial neural network model: inputting labeled three-dimensional images as training data into the artificial neural network model; and training the artificial neural network model as the correction factor determining network. The method for obtaining the training data for training the correction factor determining network may include: first capturing a large quantity of three-dimensional images about an imaging target (for example, various people) by using a three-dimensional camera arranged at a preset position. Furthermore, experts mark correction factors on the three-dimensional images based on experience.

A supervised learning manner may be used in the training processes of the correction factor determining network and the key point recognition network. Parameters of the artificial neural network model can be adjusted by using an optimization method (for example, stochastic gradient descent) so that an error between a prediction result of the artificial neural network model and a labeling result keeps decreasing until the error converges.

Assuming that an X-ray imaging protocol is a neck imaging protocol, the three-dimensional camera 73 photographs the to-be-detected subject 75 to acquire a three-dimensional image of the to-be-detected subject 75. The three-dimensional camera 73 sends the three-dimensional image of the to-be-detected subject 75 to the control host 60 through wired or wireless communication with the control host 60. The control host 60 determines that a predetermined key point corresponding to the neck imaging protocol is a laryngeal prominence point.

The key point recognition network in the control host 60 recognizes a laryngeal prominence point B located on a surface of the to-be-detected subject 75 in the three-dimensional image of the to-be-detected subject 75. The control host 60 determines a distance SOSD2 between a light source of the three-dimensional camera 73 and the recognized laryngeal prominence point B by using a distance measurement algorithm, and determines three-dimensional coordinates of the laryngeal prominence point B in a coordinate system of the three-dimensional camera 73 based on the SOSD2. The control host 60 determines three-dimensional coordinates of the laryngeal prominence point B in a coordinate system of the X-ray generation assembly based on the three-dimensional coordinates of the laryngeal prominence point B in the coordinate system of the three-dimensional camera 73 and based on a transformation matrix between the coordinate system of the three-dimensional camera 73 and the coordinate system of the X-ray generation assembly. The control host 60 then determines a distance SOSD1 between the X-ray source and the laryngeal prominence point B by using the three-dimensional coordinates of the laryngeal prominence point B in the coordinate system of the X-ray generation assembly.

The control host 60 stores preset parameters of the neck imaging protocol. The preset parameters include a SID and a TDD. Herein, a distance between the X-ray source and an imaging plane of the flat panel detector 90 is the SID, and a distance between a panel 91 (that is, a touch panel) of the film holder assembly 78 and the flat panel detector 90 in the film holder assembly 78 is the TDD. The correction factor determining network in the control host 60 determines a correction factor $\gamma$ of the three-dimensional image of the to-be-detected subject 75. A TOD is a distance between a neck reference line 92 of the to-be-detected subject 75 and the panel 91 of the film holder assembly 78. The control host 60 calculates the TOD, where TOD=$\gamma$*(SID–TDD–SOSD1).

The three-dimensional camera 73 may not be arranged on the ceiling 70. For example, the three-dimensional camera 73 may be arranged at an installation position 82 on a housing of the beam limiting device 72, to help the X-ray source coincide with the light source of the three-dimensional camera 73. When the X-ray source coincides with the light source of the three-dimensional camera 73, the control host 60 calculates the TOD, where TOD=γ *(SID−TDD−SOSD1). In this case, the control host 60 determines the distance SOSD1 between the light source of the three-dimensional camera 73 and the recognized laryngeal prominence point B by using the distance measurement algorithm. SOSD1 is also the distance between the X-ray source and the laryngeal prominence point B.

The panel 91 of the film holder assembly 78 can be detected in a target detection manner in the three-dimensional image captured by the three-dimensional camera 73. A first identifier in a predetermined three-dimensional shape is generated at a position of the panel 91 of the film holder assembly 78 in the three-dimensional image. Furthermore, a second identifier is generated in a region in which the to-be-detected subject 75 is located in the three-dimensional image. A distance between the first identifier and the second identifier is a product of a calculated TOD and a scale ratio of the three-dimensional image.

In a BWS mode during non-whole spine imaging, the to-be-detected subject 75 approaches the film holder assembly 78. The difference lies in that, in a BWS mode during whole spine imaging, the to-be-detected subject 75 does not directly approach the film holder assembly 78 but stands on a supporting plate 98.

Figure 5:
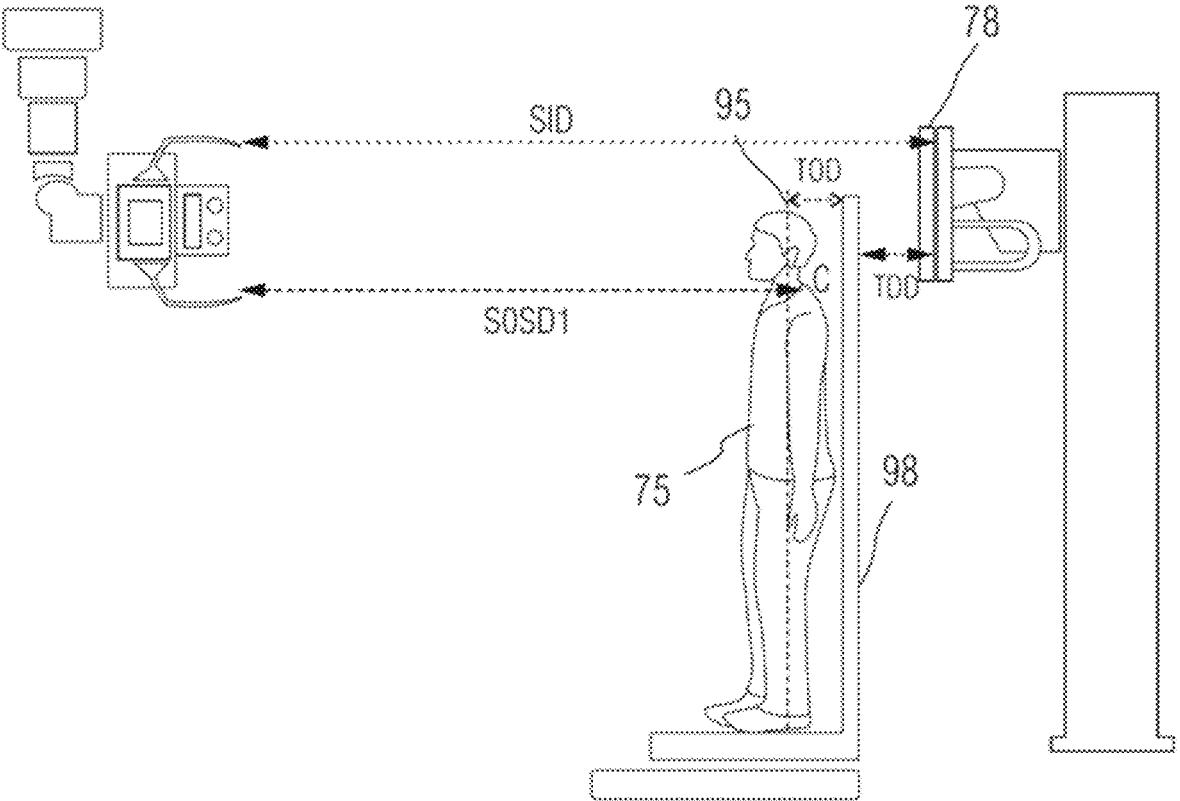
FIG. 5 is a schematic diagram of an example of determining a TOD in a whole spine scan according to an implementation of the present disclosure.

FIG. 5 is a schematic diagram of an example of determining a TOD in a whole spine scan according to an implementation of the present disclosure.

It can be seen from FIG. 5 that a to-be-detected subject 75 stands on a supporting plate 98. A predetermined key point corresponding to the whole spine scan is a shoulder C (the left shoulder or the right shoulder). A distance between an X-ray source and an imaging plane of a flat panel detector in a film holder assembly 78 is a SID. A distance between the supporting plate 98 and the flat panel detector in the film holder assembly 78 is a TDD. A distance between a spine reference line 95 and the supporting plate 98 is a TOD.

Figure 6:
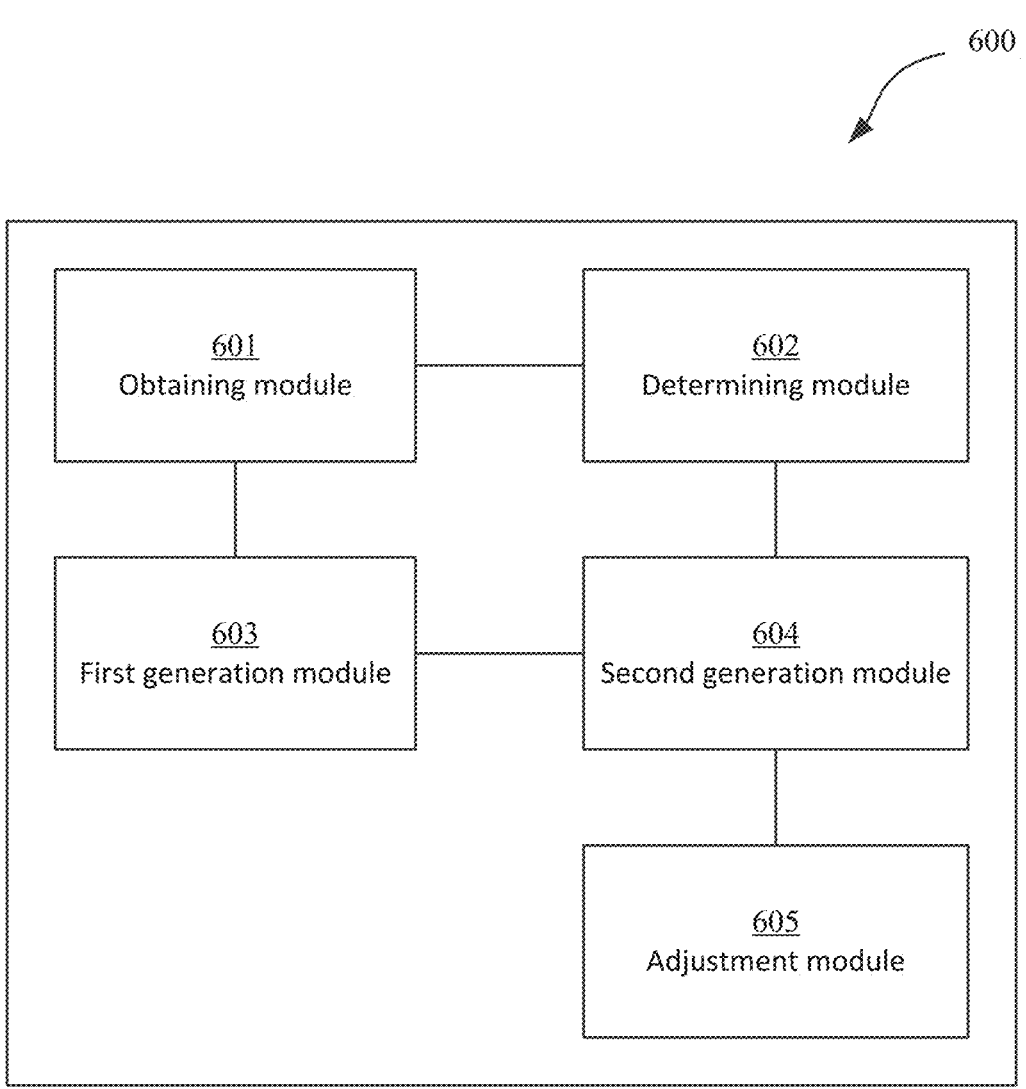
FIG. 6 is a structural diagram of an apparatus for visualization of a TOD in X-ray imaging according to an implementation of the present disclosure.

Based on the foregoing descriptions, the implementations of the present disclosure further provide an apparatus for visualization of a TOD in X-ray imaging. FIG. 6 is a structural diagram of an apparatus for visualization of a TOD in X-ray imaging according to an implementation of the present disclosure.

As shown in FIG. 6, an apparatus 600 includes:

an obtaining module 601, configured to obtain a three-dimensional image of a to-be-detected subject that includes an object;

a determining module 602, configured to determine a TOD;

a first generation module 603, configured to generate a first identifier at a position of a touch panel in the three-dimensional image; and a second generation module 604, configured to generate a second identifier in the three-dimensional image, where a distance between the first identifier and the second identifier corresponds to the TOD.

In an implementation, the first generation module 603 is configured to determine a SID and a TDD based on an X-ray imaging protocol: determine the position of the touch panel in the three-dimensional image based on the SID and the TDD; and generate the first identifier in a predetermined three-dimensional shape at the position of the touch panel in the three-dimensional image.

In an implementation, the first generation module 603 is configured to detect the touch panel in the three-dimensional image in a target detection manner; and generate the first identifier in a predetermined three-dimensional shape at the position of the touch panel in the three-dimensional image.

In an implementation, the determining module 602 is configured to determine a SID and a TDD; and determine, based on the three-dimensional image, a distance between a light source of a camera assembly and a predetermined key point located on a surface of the to-be-detected subject, where the predetermined key point corresponds to an X-ray imaging protocol; and determine the TOD based on the SID, the TDD, and the distance between the light source of the camera assembly and the predetermined key point.

In an implementation, the determining module 602 is configured to input the three-dimensional image into a key point recognition network: enable the key point recognition network to recognize the predetermined key point located on the surface of the to-be-detected subject in the three-dimensional image; and determine, based on a distance measurement algorithm, the distance between the light source of the camera assembly and the recognized predetermined key point.

In an implementation, an X-ray source coincides with the light source of the camera assembly; and the determining module 602 is configured to determine the TOD, where TOD=γ*(SID−TDD−SOSD1), SID is the source to image distance, TDD is the touch panel to detector distance, SOSD1 is the distance between the light source of the camera assembly and the predetermined key point, and γ is a correction factor.

In an implementation, an X-ray source does not coincide with the light source of the camera assembly; and that the determining module 602 is configured to determine the TOD includes: determining a distance SOSD1 between the X-ray source and the predetermined key point based on the distance SOSD2 between the light source of the camera assembly and the predetermined key point; and determining the TOD, where TOD=γ*(SID−TDD−SOSD1), SID is the source to image distance, TDD is the touch panel to detector distance, and γ is a correction factor.

In an implementation, an adjustment module 605 is further included and configured to receive a user instruction; and adjust at least one of the following based on the user instruction: a shape of the first identifier: a position of the first identifier: a shape of the second identifier; and a position of the second identifier.

In an implementation, the second generation module 604 is further configured to determine a product of the TOD and a scale ratio of the three-dimensional image as the distance between the first identifier and the second identifier. For example, assuming that the height of the to-be-detected subject in the three-dimensional image is 10 cm, and the height of the to-be-detected subject in the real world is 180 cm, the scale ratio of the three-dimensional image is 10:180. Assuming that the TOD is 20 cm, the distance between the first identifier and the second identifier in the three-dimensional image is: 20*(10/180) cm, that is, 1.11 cm.

Figure 7:
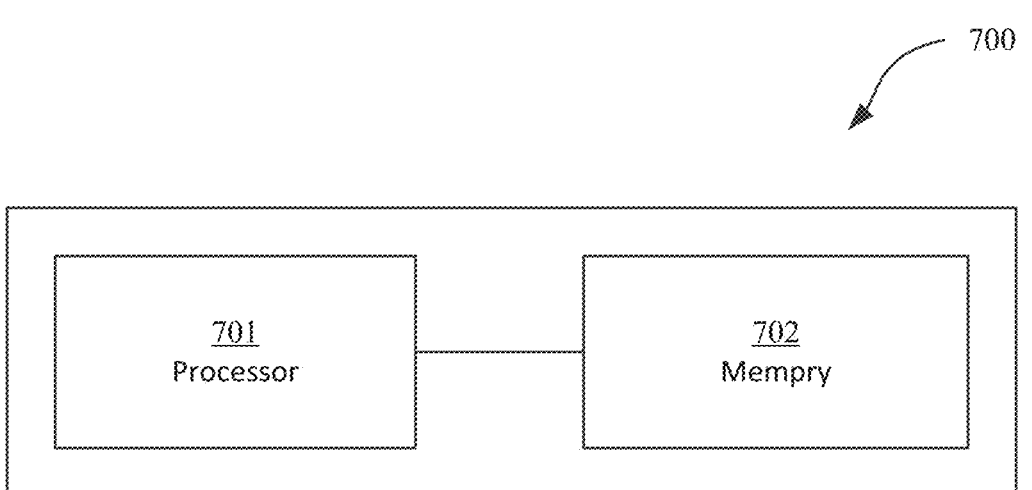
FIG. 7 is a structural diagram of an apparatus that has a memory-processor architecture and is for visualization of a TOD in X-ray imaging according to an implementation of the present disclosure.

FIG. 7 is a structural diagram of an apparatus that has a memory-processor architecture and is for visualization of a TOD in X-ray imaging according to an implementation of the present disclosure.

As shown in FIG. 7, an apparatus 700 for visualization of a TOD in X-ray imaging includes a processor 701, a memory 702, and a computer program stored on the memory 702 and executable on the processor 701. The computer program, when executed by the processor 701, implements any one of the foregoing methods for visualization of a TOD in X-ray imaging. The memory 702 may be specifically implemented as various storage media, such as an electrically erasable programmable read-only memory (EEPROM), a flash memory, and a programmable read-only memory (PROM). The processor 701 may be implemented to include one or more central processing units (CPUs) or implemented as one or more field programmable gate arrays. The field programmable gate array integrates one or more CPU cores. Specifically, the CPU or the CPU core may be implemented as a CPU, a microcontroller unit (MCU), a digital signal processing (DSP), or the like.

It should be noted that not all steps and modules in the procedures and the structural diagrams are necessary, and some steps or modules may be omitted according to an actual requirement. An execution sequence of the steps is not fixed and may be adjusted according to needs. Division of the modules is merely functional division for ease of description. During actual implementation, one module may be implemented separately by a plurality of modules, and functions of the plurality of modules may alternatively be implemented by the same module. The modules may be located in the same device or in different devices.

Hardware modules in the implementations may be implemented in a mechanical manner or an electronic manner. For example, a hardware module may include specially designed permanent circuits or logic devices (for example, an application-specific processor such as an FPGA or an ASIC) to complete specific operations. The hardware module may also include temporarily configured programmable logic devices or circuits (for example, including a universal processor or another programmable processor) to perform specific operations. The hardware module is implemented by specifically using the mechanical manner, using the application-specific permanent circuits, or using the temporarily configured circuits (for example, configured by software), which can be decided according to consideration of costs and time.

The present disclosure further provides a machine-readable storage medium, which stores instructions that are used to make a machine to execute the instructions of the method described in this specification. Specifically, a system or an apparatus that is equipped with a storage medium may be provided. The storage medium stores software program code that implements functions of any implementation in the foregoing embodiments, and a computer (a CPU or an MPU) of the system or the apparatus is enabled to read and execute the program code stored in the storage medium. In addition, a program code based instruction may also be used to enable an operating system or the like running in the computer to complete some or all actual operations. The program code read from the storage medium may also be written into a memory that is disposed in an expansion board inserted in the computer or may be written into a memory that is disposed in an expansion unit connected to the computer, and then a CPU or the like that is installed on the expansion board or expansion unit may be enabled to execute some or all actual operations based on the instructions of the program code, so as to implement the functions of any one of the foregoing implementations. Implementations of the storage medium for providing the program code may include a floppy disk, a hard disk, a magneto-optical disk, an optical memory (such as a CD-ROM, a CD-R, a CD-RW, a DVD-ROM, a DVD-RAM, a DVD-RW, and a DVD+RW), a magnetic tape, a non-volatile storage card, and a ROM. Optionally, the program code may be downloaded from a server computer or a cloud by using a communication network.

The foregoing descriptions are merely preferred implementations of the present disclosure and are not intended to limit the protection scope of the present disclosure. Any modification, equivalent replacement, or improvement made within the spirit and principle of the present disclosure shall fall within the protection scope of the present disclosure.

What is claimed is:

1. An apparatus for a visualization of a touch panel-to-object distance (TOD) in X-ray imaging, comprising:
    an obtaining module operable to obtain a three-dimensional image of a to-be-detected subject that comprises an object;
    a determining module operable to determine a TOD;
    a first generation module operable to generate a first identifier at a position of a touch panel in the three-dimensional image of the to-be-detected subject; and
    a second generation module operable to generate a second identifier in the three-dimensional image of the to-be-detected subject, wherein a distance between the first identifier and the second identifier corresponds to the TOD.

2. The apparatus according to claim 1, wherein the first generation module is further operable to:
    determine a source-to-image distance (SID) and a touch panel-to-detector distance (TDD) based on an X-ray imaging protocol;
    determine the position of the touch panel in the three-dimensional image based on the SID and the TDD; and
    generate the first identifier in a predetermined three-dimensional shape at the position of the touch panel in the three-dimensional image.

3. The apparatus according to claim 1, wherein the first generation module is further operable to:
    detect the touch panel in the three-dimensional image in a target detection manner; and
    generate the first identifier in a predetermined three-dimensional shape at the position of the touch panel in the three-dimensional image.

4. The apparatus according to claim 1, wherein the determining module is further operable to:
    determine a source-to-image distance (SID) and a touch panel-to-detector distance (TDD);
    determine, based on the three-dimensional image, a distance between a light source of a camera assembly and a predetermined key point located on a surface of the to-be-detected subject, wherein the predetermined key point corresponds to an X-ray imaging protocol; and
    determine the TOD based on the SID, the TDD, and the distance between the light source of the camera assembly and the predetermined key point.

5. The apparatus according to claim 4, wherein the determining module is further operable to:
    input the three-dimensional image into a key point recognition network;
    enable the key point recognition network to recognize the predetermined key point located on the surface of the to-be-detected subject in the three-dimensional image; and
    determine, based on a distance measurement algorithm, a distance between the light source of the camera assembly and the recognized predetermined key point.

6. The apparatus according to claim 4, wherein an X-ray source coincides with the light source of the camera assembly, and the determining module is further operable to determine the TOD, wherein TOD=γ*(SID−TDD−SOSD1), SID is the source-to-image distance, TDD is the touch panel-to-detector distance, SOSD1 is the distance between the light source of the camera assembly and the predetermined key point, and γ is a correction factor; or an X-ray source does not coincide with the light source of the camera assembly, and the determining module is further operable to:

determine a distance SOSD1 between the X-ray source and the predetermined key point based on a distance SOSD2 between the light source of the camera assembly and the predetermined key point; and determine the TOD, wherein TOD=γ*(SID−TDD−SOSD1), SID is the source-to-image distance, TDD is the touch panel-to-detector distance, and γ is a correction factor.

7. The apparatus according to claim 1, further comprising:

an adjustment module operable to receive a user instruction, and adjust, based on the user instruction, a shape of the first identifier, a position of the first identifier, a shape of the second identifier, or a position of the second identifier.

8. The apparatus according to claim 1, wherein the second generation module is further operable to determine a product of the TOD and a scale ratio of the three-dimensional image as the distance between the first identifier and the second identifier.

9. A method for a visualization of a touch panel to object distance (TOD) in X-ray imaging, comprising:

obtaining a three-dimensional image of a to-be-detected subject that comprises an object;

determining a TOD;

generating a first identifier at a position of a touch panel in the three-dimensional image of the to-be-detected subject; and generating a second identifier in the three-dimensional image of the to-be-detected subject, wherein a distance between the first identifier and the second identifier corresponds to the TOD.

10. The method according to claim 9, wherein the generating the first identifier at the position of the touch panel in the three-dimensional image comprises:

determining a source-to-image distance (SID) and a touch panel-to-detector distance (TDD) based on an X-ray imaging protocol;

determining the position of the touch panel in the three-dimensional image based on the SID and the TDD; and generating the first identifier in a predetermined three-dimensional shape at the position of the touch panel in the three-dimensional image.

11. The method according to claim 9, wherein the generating the first identifier at the position of the touch panel in the three-dimensional image comprises:

detecting the touch panel in the three-dimensional image in a target-detection manner; and generating the first identifier in a predetermined three-dimensional shape at the position of the touch panel in the three-dimensional image.

12. The method according to claim 9, wherein the determining a TOD comprises:

determining a source-to-image distance (SID) and a touch panel-to-detector distance (TDD);

determining, based on the three-dimensional image, a distance between a light source of a camera assembly and a predetermined key point located on a surface of the to-be-detected subject, wherein the predetermined key point corresponds to an X-ray imaging protocol; and determining the TOD based on the SID, the TDD, and the distance between the light source of the camera assembly and the predetermined key point.

13. The method according to claim 12, wherein the determining, based on the three-dimensional image, the distance between the light source of the camera assembly and the predetermined key point located on the surface of the to-be-detected subject comprises:

inputting the three-dimensional image into a key point recognition network;

enabling the key point recognition network to recognize the predetermined key point located on the surface of the to-be-detected subject in the three-dimensional image; and determining, based on a distance measurement algorithm, a distance between the light source of the camera assembly and the recognized predetermined key point.

14. The method according to claim 12, wherein an X-ray source coincides with the light source of the camera assembly; and the determining the TOD based on the SID, the TDD, and the distance between the light source of the camera assembly and the predetermined key point comprises:

determining the TOD, wherein TOD=γ*(SID−TDD−SOSD1), SID is the source-to-image distance, TDD is the touch panel-to-detector distance, SOSD1 is the distance between the light source of the camera assembly and the predetermined key point, and γ is a correction factor; or an X-ray source does not coincide with the light source of the camera assembly; and the determining the TOD based on the SID, the TDD, and the distance between the light source of the camera assembly and the predetermined key point comprises: determining a distance SOSD1 between the X-ray source and the predetermined key point based on a distance SOSD2 between the light source of the camera assembly and the predetermined key point; and determining the TOD, wherein TOD=γ*(SID−TDD−SOSD1), SID is the source-to-image distance, TDD is the touch panel-to-detector distance, and γ is a correction factor.

15. The method according to claim 9, further comprising:

receiving a user instruction; and adjusting, based on the user instruction, a shape of the first identifier, a position of the first identifier, a shape of the second identifier, or a position of the second identifier.

16. The method according to claim 9, further comprising:

determining a product of the TOD and a scale ratio of the three-dimensional image as the distance between the first identifier and the second identifier.

17. An apparatus for a visualization of a touch panel to object distance (TOD) in X-ray imaging, comprising:

a processor; and a memory, wherein the memory is operable to store an application program executable by the processor, and the application program is operable to enable the processor to perform the method for a visualization of a TOD in X-ray imaging according to claim 9.

18. A non-transitory computer-readable storage medium storing computer-readable instructions to perform the method for a visualization of a TOD in X-ray imaging according to claim 9.

* * * * *